(12) United States Patent
Peters et al.

(10) Patent No.: US 7,335,526 B2
(45) Date of Patent: Feb. 26, 2008

(54) SENSING SYSTEM

(75) Inventors: Kevin F Peters, Corvallis, OR (US); Xiaofeng Yang, Corvallis, OR (US)

(73) Assignee: Hewlett-Packard Development Company, L.P., Houston, TX (US)

(*) Notice: Subject to any disclaimer, the term of this patent is extended or adjusted under 35 U.S.C. 154(b) by 0 days.

(21) Appl. No.: 11/263,788

(22) Filed: Oct. 31, 2005

(65) Prior Publication Data

US 2007/0099351 A1    May 3, 2007

(51) Int. Cl.
*H01L 21/02* (2006.01)
(52) U.S. Cl. .......... 438/49; 438/48; 257/414; 257/E21.02; 977/937; 977/957
(58) Field of Classification Search ........ 257/29, 257/414, E21.02, E21.04; 438/48, 49; 977/762, 977/882–883, 932, 936–937, 953, 957
See application file for complete search history.

(56) References Cited

U.S. PATENT DOCUMENTS

| | | | |
|---|---|---|---|
| 6,674,932 B1* | 1/2004 | Zhang et al. | 385/16 |
| 7,091,096 B2* | 8/2006 | Balasubramanian et al. | 438/292 |
| 2002/0122766 A1* | 9/2002 | Lieber et al. | 423/447.3 |
| 2003/0134433 A1 | 7/2003 | Gabriel | |
| 2003/0215865 A1* | 11/2003 | Mayer et al. | 435/6 |
| 2004/0022718 A1* | 2/2004 | Stupp et al. | 423/445 R |
| 2004/0043527 A1* | 3/2004 | Bradley et al. | 438/48 |
| 2004/0048241 A1* | 3/2004 | Freeman et al. | 435/5 |
| 2004/0132070 A1* | 7/2004 | Star et al. | 435/6 |
| 2004/0235016 A1* | 11/2004 | Hamers et al. | 435/6 |
| 2004/0253741 A1* | 12/2004 | Star et al. | 436/150 |
| 2005/0129573 A1* | 6/2005 | Gabriel et al. | 422/58 |
| 2005/0244811 A1* | 11/2005 | Soundarrajan et al. | 435/4 |
| 2005/0265914 A1* | 12/2005 | Gu et al. | 423/445 B |
| 2006/0054936 A1* | 3/2006 | Lieber et al. | 257/210 |
| 2006/0055392 A1* | 3/2006 | Passmore et al. | 324/71.1 |
| 2006/0078468 A1* | 4/2006 | Gabriel et al. | 422/88 |
| 2006/0125033 A1* | 6/2006 | Segal et al. | 257/415 |
| 2006/0269927 A1* | 11/2006 | Lieber et al. | 435/6 |
| 2006/0273356 A1* | 12/2006 | Matsumoto et al. | 257/253 |

FOREIGN PATENT DOCUMENTS

WO    WO 03/078652    9/2003

OTHER PUBLICATIONS

Cronin, S. B. et al. "Electrochemical Gating of Individual Single-Wall Carbon Nanotubes Observed By Electron Transport Measurements and Resonant Raman Spectroscopy." Appl. Phys. Lett. vol. 84 (2004): 2052-2054.*
Balasubramanian, K. et al. "A Selective Electrochemical Approach to Carbon Nanotube Field-Effect Transistors." NANOLETT. vol. 4 (2004): 827-830.*
Kruger, M. et al. "Electrochemical Carbon Nanotube Field-Effect Transistor." Appl. Phys. Lett. vol. 78 (2001): 1291-1293.*

(Continued)

*Primary Examiner*—B. William Baumeister
*Assistant Examiner*—Matthew W. Such
(74) *Attorney, Agent, or Firm*—Matthew L. Wade

(57) ABSTRACT

A ChemFET Sensing system is Described.

28 Claims, 12 Drawing Sheets

OTHER PUBLICATIONS

Kruger, M. et al. "Sensitivity of Single Multiwalled Carbon Nanotubes to the Environment." New J. Phys. vol. 5 (2003): 138.1-138.11.*

Someya, T. et al. "Conductance Measurement of Single-Walled Carbon Nanotubes in Aqueous Environment." Appl. Phys. Lett. vol. 82 (2003): 2338-2340.*

Gruner, G. "Carbon Nanotube Transistors for Biosensing Applications." Anal. Bioanal. Chem. vol. 384 (2006): 322-335.*

International Search Report dated Nov. 16, 2006 for PCT/US2006/029731, Hewlett-Packard (3 pages).

Heller, I. et al: "Individual Single-Walled Carbon Nanotubes as Nanoelectrodes for Electrochemistry", Nano Letters, vol. 5, No. 1, Dec. 17, 2004, pp. 137-142.

Li, Z. et al: "Sequence-Specific Label-Free DNA Sensors Based on Silicon Nanowires", Nano Letters, vol. 4, No. 2, Jan. 8, 2004, pp. 245-247.

* cited by examiner

SENSING SYSTEM

BACKGROUND

Chemical and biological sensing systems are important in a number of different applications, such as medical, environmental, agricultural, military and industrial applications, to name a few. ChemFET sensing systems based on chemically sensitive field effect transistors have in particular been investigated for decades and have demonstrated some commercial applicability, although mainly for pH and pH-mediated enzyme sensors (EnFETs) because of the immense technical difficulties involved in the species-specific, highly sensitive biochemical sensing that is needed for biotech and medical usage.

One type of ChemFET sensing system employs a nanowire sensing element that is functionalized (with a functional agent) to enable the nanowire to electrically respond to the presence of an analyte in a sample. Interaction between the functionalized nanowire and the analyte may cause, for example, the generation of an electric field that, in turn, causes a detectable change in an electrical property of the nanowire (e.g., a detectable shift in electrical conductance). This type of ChemFET sensing system may alternatively be referred to herein as a "nanowire based" sensing system. Examples of a "nanowire based" sensing system are described in the patent literature. See, for example, PCT Application WO 02/48701, having international filing date of Dec. 11, 2001, entitled "NANOSENSORS", by inventors Lieber et.al.

Nanowire based sensing systems offer a number of advantages including very high sensitivity and the ability to monitor very small sample sizes. There is a need, however, to improve upon the manufacturability of these sensing systems and to expand their capabilities.

DESCRIPTION

Figure 1:
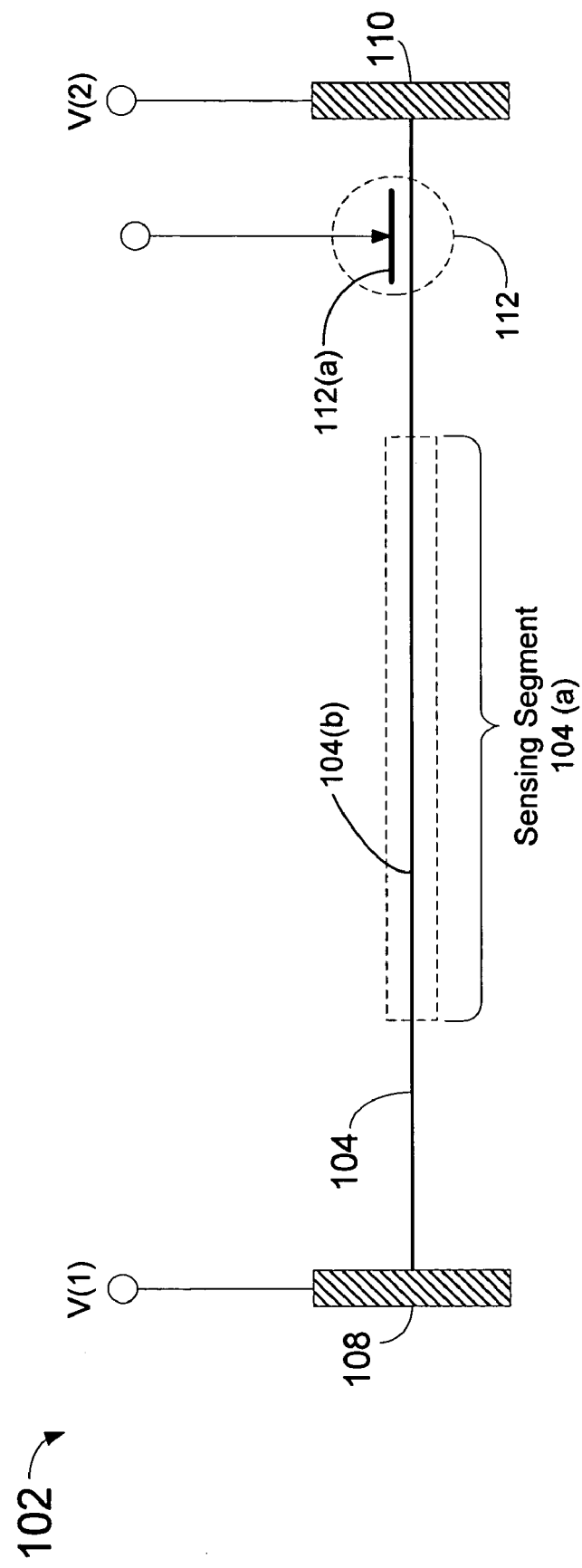
FIG. 1 is a high-level schematic diagram of a nanowire based sensing system.

In the following detailed description, numerous specific details are set forth to provide a thorough understanding of claimed subject matter. However, it will be understood by those skilled in the art that claimed subject matter may be practiced without these specific details. In other instances, well-known methods, procedures, components and/or circuits have not been described in detail so as not to obscure claimed subject matter.

As used herein, a "nanowire" is an elongated nanoscale structure which, along its length, includes a cross-sectional dimension that is less than 1000 nanometers. The cross-section of a nanowire, in various embodiments, may be any regular shape, such as (but not limited to) square, rectangular, elliptical, trapezoidal or some other regular shape. The cross section of a nanowire, in other embodiments, may have an irregular shape.

As used herein, the term "Nanowire" may also be used to refer to the elongated sidewall surfaces described in the U.S. patent application Ser. No. 11/263,786, filed Oct. 31, 2005, entitled "SENSOR", by inventor Kevin Peters. The disclosure of that application is incorporated herein by reference.

A nanowire, in various embodiments, may be a semiconductor and may be formed from any number of different materials, such as Si, Si-alloys, Ge, GaAs, metals, nitrides, and/or oxides, to name a few. Also, combinations of the above materials may be employed, such as an Si core with a cladding of oxide and/or nitride.

In various embodiments, any number of different methods may be employed to fabricate a nanowire including examples and combinations of the following: imprinting, lithography, chemical vapor deposition (CVD), etching, laser ablation, arc discharge, and/or electrochemical methods. It should be clear that these particular examples are not intended to limit the scope of claimed subject matter. By way of one non-limiting example, nanowires in various embodiments may be fabricated utilizing the techniques described in U.S. patent application Ser. No. 10/423,063, filed Apr. 24, 2003, entitled "SENSOR PRODUCED USING IMPRINT LITHOGRAPHY", to Kevin Peters and James Stasiak.

The process of coating a nanowire with a "functional agent" may be referred to herein as "functionalization". Functional agents may, for example, bind specific chemical and/or biological species of interest, such as, for example, thiol groups, nucleic acids (deoxyribonucleic acid or "DNA", peptide nucleic acids or "PNA", and Ribonucleic acid or "RNA"), aptamers, hormones, carbohydrates, proteins, antibodies, antigens, molecular receptors, and/or cellular surface binding sites, to provide a few biochemical examples. Some functional agents may bind other functional agents. For example, a first electrodeposited gold functional agent may bind a thiol-terminated DNA functional agent that may, in turn, bind a complementary DNA species of interest. Another example is a first DNA functional agent that binds a second PNA functional agent that may, in turn, bind a complementary DNA species of interest.

It is also noted that functional agents are not limited to binding of specific species. Also, not binding non-specific species may be another function of a functional agent. As one example, without loss of generality, the use of so-called anti-fouling functional agents may inhibit the binding of a species to a nanowire surface. Another kind of functional agent may inhibit binding until such time when a condition is changed, such as (but not limited to) pH, temperature, or oxidation state, whereupon binding is no longer inhibited. Another kind of functional agent may serve to perform enzymatic activity, such as catalysis of a reaction, as with lactase dehydrogenase. These are merely examples of the functions of functional agents and are not intended to limit the scope of claimed subject matter.

Sensing System Embodiment

FIG. 1 is a high-level schematic diagram of a nanowire based (CHEMFET) sensing system 102 that incorporates one example embodiment of the invention. In general, the sensing system 102 may be used to detect the presence of an analyte in a sample. As indicated, the sensing system 102 includes a nanowire sensing element (nanowire) 104, a first electrode 108, a second electrode 110 and a Field Effect Transistor (FET) 112.

The nanowire 104 is, in this example, a continuous structure that bridges the two contact electrodes (108, 110) which, in turn, respectively provide contact points for a power supply system (not shown) and a monitor (also not shown). The monitor may be capable of monitoring an electrical property of the nanowire 104, such as electrical conductance or resistance. The nanowire 104 may be formed, for example, from a thin layer of semiconductor material and may be disposed on an insulating material. According to one embodiment, for example, the nanowire 104 may be fabricated utilizing a commercially available SOI (silicon on insulator) wafer.

It is noted for the following discussion, that the nanowire 104 includes, along a particular segment 104($a$) of its length, an exposed surface area that is intended to be functionalized in order to enable the nanowire 104 to electrically respond to the presence of an analyte in a fluid sample (not shown). For ease of discussion, we may refer to this particular segment of the nanowire 104 as the "nanowire sensing segment" 104($a$).

In one embodiment, the sensing system may include a fluid handling system (not shown) that can be used to expose the nanowire sensing segment to one or more fluids in the course of a functionalization process or during a sensing operation. The fluid may have a chemical potential and more specifically an electrochemical potential that, in the continuing embodiment, is well-established. One common way of establishing the electrochemical potential is by contacting the fluid to a reference electrode, in most cases at a remote position from the nanowire sensing segment. Suitable reference electrodes include (but are not limited to) platinum, palladium, gold, silver, silver with silver chloride, calumel, a standard hydrogen reference cell, and others that are well known to persons skilled in electrochemistry. Accordingly, an electrochemical potential difference between the fluid and the exposed surface area of the nanowire sensing segment can be established by applying an electrical potential between the reference electrode and the first electrode 108. The (electro)chemical potential difference is well known to influence reactions including oxidation, reactivity, binding, diffusion, ionic diffusion, and electrophoresis.

As indicated schematically in FIG. 1, the FET 112 includes a gate electrode 112($a$) that is positioned over a region of the nanowire that is between the nanowire sensing segment 104($a$) and the second electrode 110. A suitable dielectric material (not shown) may be disposed between the gate electrode 112($a$) and the nanowire 104. Moreover, the FET 112 enables the sensing system 102 to generate an electric field that has the effect of preventing (or "gating") electric current from passing (through the body of the nanowire 104) between the nanowire "sensing segment" 104($a$) and the second electrode 110. In this manner, the FET 112 enables the sensing system 102 to electrically disconnect the nanowire sensing segment 104($a$) from the second electrode 110. While, however, the nanowire sensing segment 104($a$) is disconnected in this manner from the second electrode 110, it remains electrically connected (through the body of the nanowire 104) to the first electrode 108. As a result, the potential of the nanowire sensing segment 104($a$) tends to float to a uniform potential that is equal to the potential of the first electrode 108.

The ability (provided by the FET 112) to electrically disconnect the sensing segment 104($a$) from the second electrode 110 may be useful for a number of purposes and it is to be understood that embodiments of the sensing system are not limited to any particular purpose. By way of example, however, such ability may be useful in a process to functionalize the nanowire sensing segment 104($a$). This proposition is illustrated further, by way of non-limiting examples, in the next part of this discussion.

Exemplary Process to Functionalize Nanowire

Figure 2:
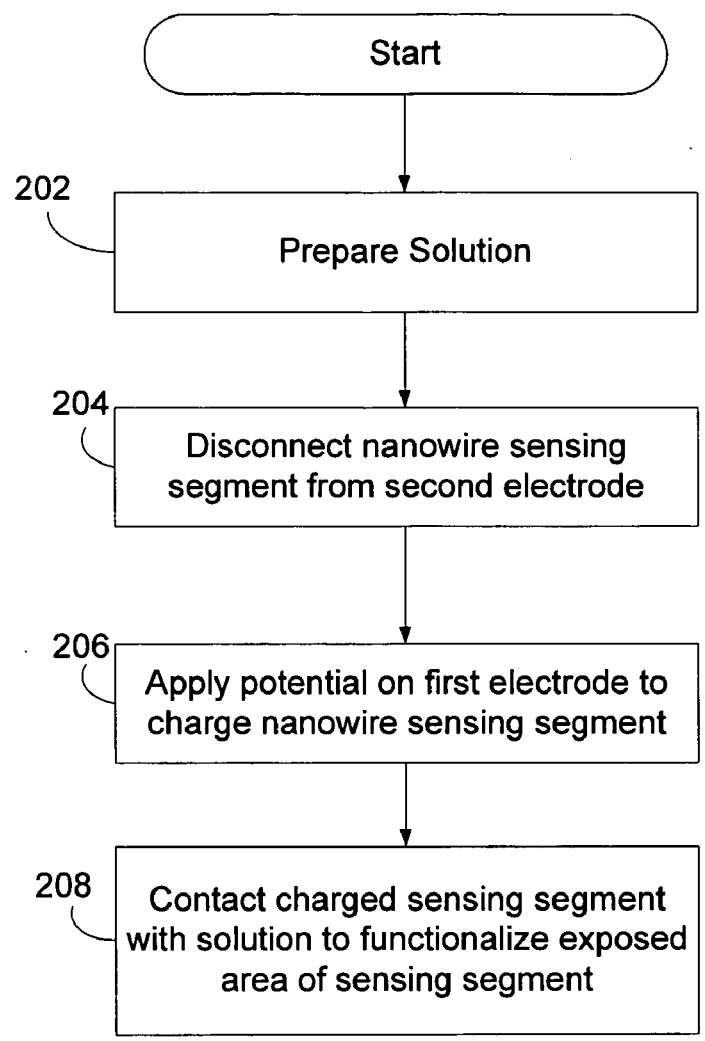
FIG. 2 is a flow diagram illustrating a process that may be followed to functionalize ananowire sensing segment according to an embodiment of the invention.

FIG. 2 is a flow diagram illustrating a process that may be followed to functionalize the nanowire sensing segment 104($a$) according to one embodiment of the invention. With reference now to FIG. 2, at step 202, a solution is prepared (step 202). The solution may generally be any solution capable of preferentially functionalizing a surface area when a suitable electrochemical potential difference is established with respect to the surface. Non-limiting examples of solutions that may be prepared at step 202 are provided below.

At step 204, the FET 112 is operated so as to electrically disconnect the nanowire sensing segment 104($a$) from the second electrode 110. While the sensing segment 104($a$) is electrically disconnected from the second electrode 110 in this manner, steps 206 and steps 208 are then performed.

At step 206, the nanowire sensing segment 104($a$) (including its exposed surface area) is electrically and uniformly charged to a pre-determined polarity (i.e., positive or negative) by applying a suitable voltage potential to the first electrode 108 so as to establish a suitable electrochemical potential difference as described above.

At step 208, the uniformly charged nanowire sensing segment 104($a$) is functionalized using the prepared solution. This final step involves placing the solution and the charged segment in contact with each other and then permitting elements (e.g., functional agents) of the solution to interact with the exposed surface area of the sensing segment 104($a$).

Non-Limiting Example

According to one implementation of the process just described, electroplating is used in order to functionalize the exposed surface area of the nanowire sensing segment 104($a$) with a thin coating of one or more metals. The metal(s) may be selected, for example, so as to enable the nanowire 104 to electrically respond to the presence of certain chemical species in a fluid. For example, the metal(s) may be selected to enable the nanowire 104 to electrically respond to the presence of certain hydrocarbons and/or oxygen, in a gas sample. In other variations, for example, the metal coating may act as an adsorption substrate for one or more chemical cross-linkers (e.g., cross-linkers with a sufhydryl functional group) by which a biochemical species can be immobilized.

The solution, in this non-limiting example, is an electrolyte solution of metal-containing ionic species that is prepared (at step 202) by dissolving the one or more selected metal-containing constituents to a suitable solvent such as an aqueous buffer solution that can be used to electroplate the metal. The metal(s) selected could be any suitable/desired metal, including nickel, copper or gold, to name a few.

At step 204, the nanowire sensing segment 104(a) is disconnected from the second electrode 110. At step 206, an appropriate voltage is applied to the first electrode 108 so as to establish a suitable electrochemical potential difference as described above between the nanowire sensing segment 104 and the electrolyte solution.

At step 208, the electrolyte solution and the charged nanowire sensing segment 104(a) are brought into contact with each other in order to functionalize (via electroplating) the exposed surface area of the sensing segment 104(a) with a layer of the one or more selected metals.

Alternative Process to Functionalize Nanowire

Figure 3:
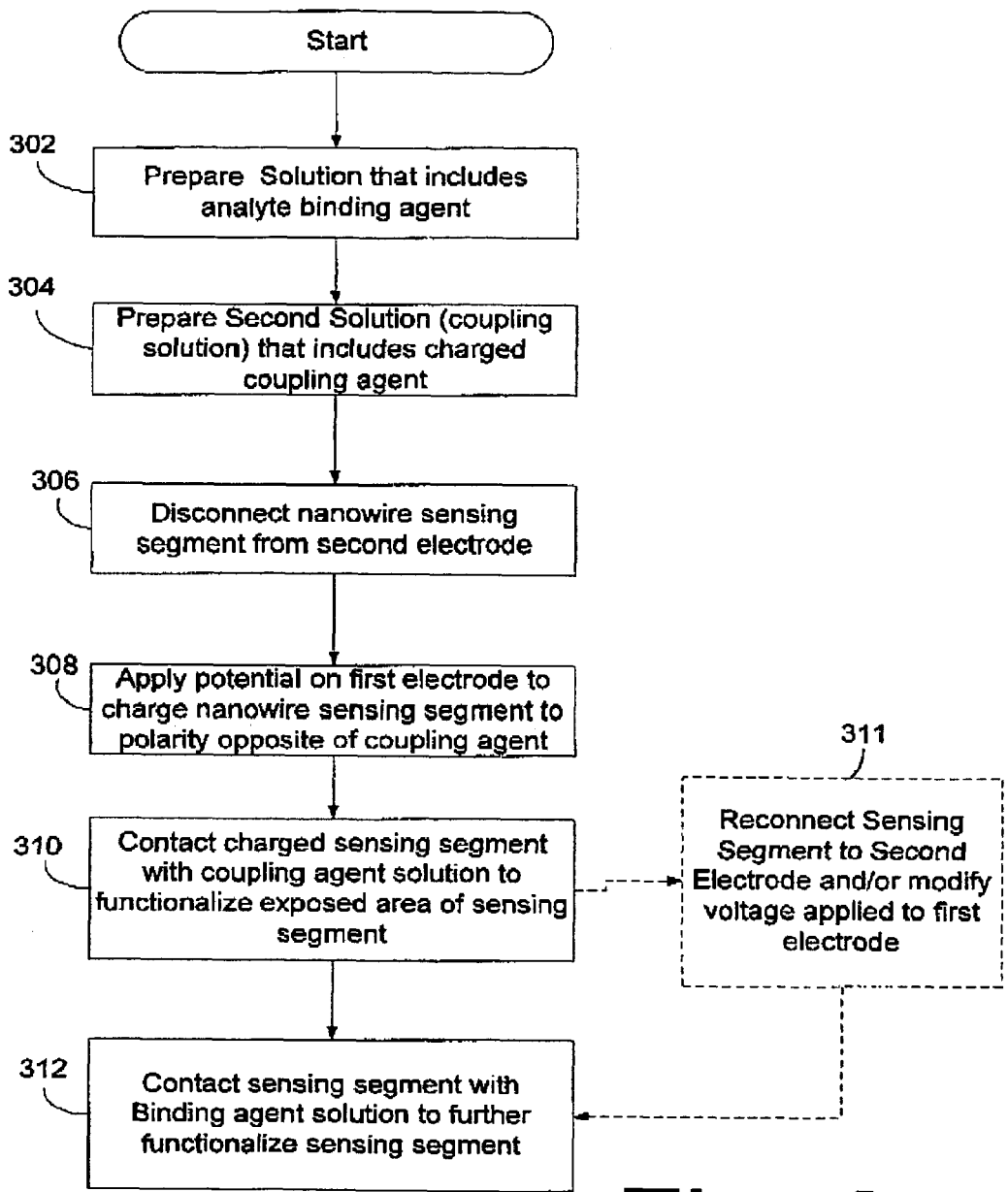
FIG. 3 is a flow diagram illustrating an alternative process that may be followed to functionalize the nanowire sensing segment according to an embodiment of the invention.

FIG. 3 is a flow diagram illustrating an alternative process that may be followed to functionalize the nanowire sensing segment 104(a) according to an embodiment of the invention. With reference now to FIG. 3, at step 302, a first solution (binding agent solution) is prepared that includes a binding agent that is capable of binding a particular analyte (target analyte) of interest.

At step 304, a second solution (coupling agent solution) is prepared that includes a coupling agent that is capable of coupling the binding agent to the exposed surface of the nanowire sensing segment 104(a). The solution is configured, in this example, so that the coupling agent in the solution is electrically charged at a pre-determined polarity (i.e., positive or negative).

At step 306, the FET 112 is operated so as to electrically disconnect the nanowire sensing element 104(a) from the second electrode 110. While the sensing segment 104(a) is electrically disconnected from the second electrode 110 in this manner, steps 308 and steps 310 are then performed.

At step 308, the sensing segment 104(a) (now disconnected from the second electrode 110) is electrically charged to a polarity that is opposite that of the coupling agent charge polarity. This step may be accomplished by applying an appropriate voltage to the first electrode 108.

At step 310, the coupling agent and the now electrically charged sensing segment 104(a) are brought into contact with each other in order to functionalize the exposed surface area of the sensing segment 104(a) with a layer of the coupling agent. As a result of the electrochemical potential difference between the solution of the charged coupling agent and the oppositely charged sensing segment 104(a), the coupling agent in the solution may migrate towards and condense preferentially onto the exposed surface area of the sensing segment 104(a). [Note that the ionic migration and/or the binding may be the effect of the electrochemical potential difference employed here and are both chemical mechanisms that are operable within embodiments of the present invention.]

At step 312, the sensing segment 104(a) (now functionalized with a layer of the coupling agent) is further functionalized with the binding agent. This step involves placing the binding agent solution in contact with the sensing segment 104(a) so as to permit the layer of the coupling agent (on the sensing segment) to immobilize the binding agent and thereby couple the binding agent to the nanowire sensing segment. It is noted that in various implementations, the sensing segment 104(a) may be connected to the second electrode 112 when step 312 is performed and/or the voltage applied to the first electrode 110 may be modified if desired.

Non-Limiting Example

In this non-limiting example, we discuss how the functionalization process just described may be performed so as to configure the nanowire 104 to detect the presence of a target DNA molecule in a sample. In this example, the binding agent is an amine terminated aptamer that is complementary to the target DNA molecule and the coupling agent is carboxylic silane.

Accordingly, step 302 may performed by preparing a binding agent solution that includes a suitable concentration of the amine terminated aptamer. Step 304 may be performed by preparing a coupling agent solution comprising carboxylic silane having a suitable PH (e.g., PH>7) that results in the carboxylic silane in the solution being deprotonated and thereby developing a negative charge. Such a solution may be prepared, for example, using Carboxyethylsilanetriol Sodium Salt which is commercially available (e.g., from Gelest, Inc.).

At step 306, the FET 112 is operated to electrically disconnect the nanowire sensing segment 104(a) from the second electrode 110. The nanowire sensing segment 104(a) remains disconnected from the second electrode 110 while steps 308-310 are performed.

At step 308, the nanowire sensing segment 104(a) is positively charged, in this example, by applying a suitable voltage to the first electrode 108. The reader will note that the polarity of the charged sensing segment is charged opposite that of the deprotonated carboxylic silane polarity. While the sensing segment 104(a) is electrically disconnected from the second electrode 110 in this manner, steps 308 and steps 310 are then performed.

At step 310, the now positively charged sensing segment 104(a) is placed in contact with the carboxylic silane acid (i.e., the coupling agent solution in this example). As a result of electrostatic forces between the negatively charged carboxylic silane in the solution and the positively charged sensing segment 104(a), the silane in the solution migrates towards and condenses onto the exposed surface of the (positively charged) sensing segment 104(a). This can result in the exposed surface of the sensing segment 104(a) being coated with a layer of the silane and, in this manner, the sensing segment 104(a) is functionalized.

At step 312, the now functionalized sensing segment is further functionalized with the binding agent. This step includes placing the binding agent solution in contact with the sensing segment so as to permit the binding agent (i.e., the amine terminated aptamers), in the solution to become immobilized by the layer of carboxylic silane on the sensing segment. As a result, the sensing segment is further functionalized with the amine terminated aptamers.

In addition to the stipulated means of establishing an electrochemical potential difference by applying a voltage between the first and reference electrodes, it is further to be understood that removing an electrochemical potential difference may also be employed in various embodiments. Whereas an ionic coupling agent or functional agent may be repelled from a surface area by application of a suitable potential, the removal of that repelling potential may result in migration and binding of said ionic agent to said surface area. The two distinct operations, based on a mechanism to attract and a mechanism not to repel, are substantially interchangeable.

Second Embodiment of a Sensing System

Figure 4A:
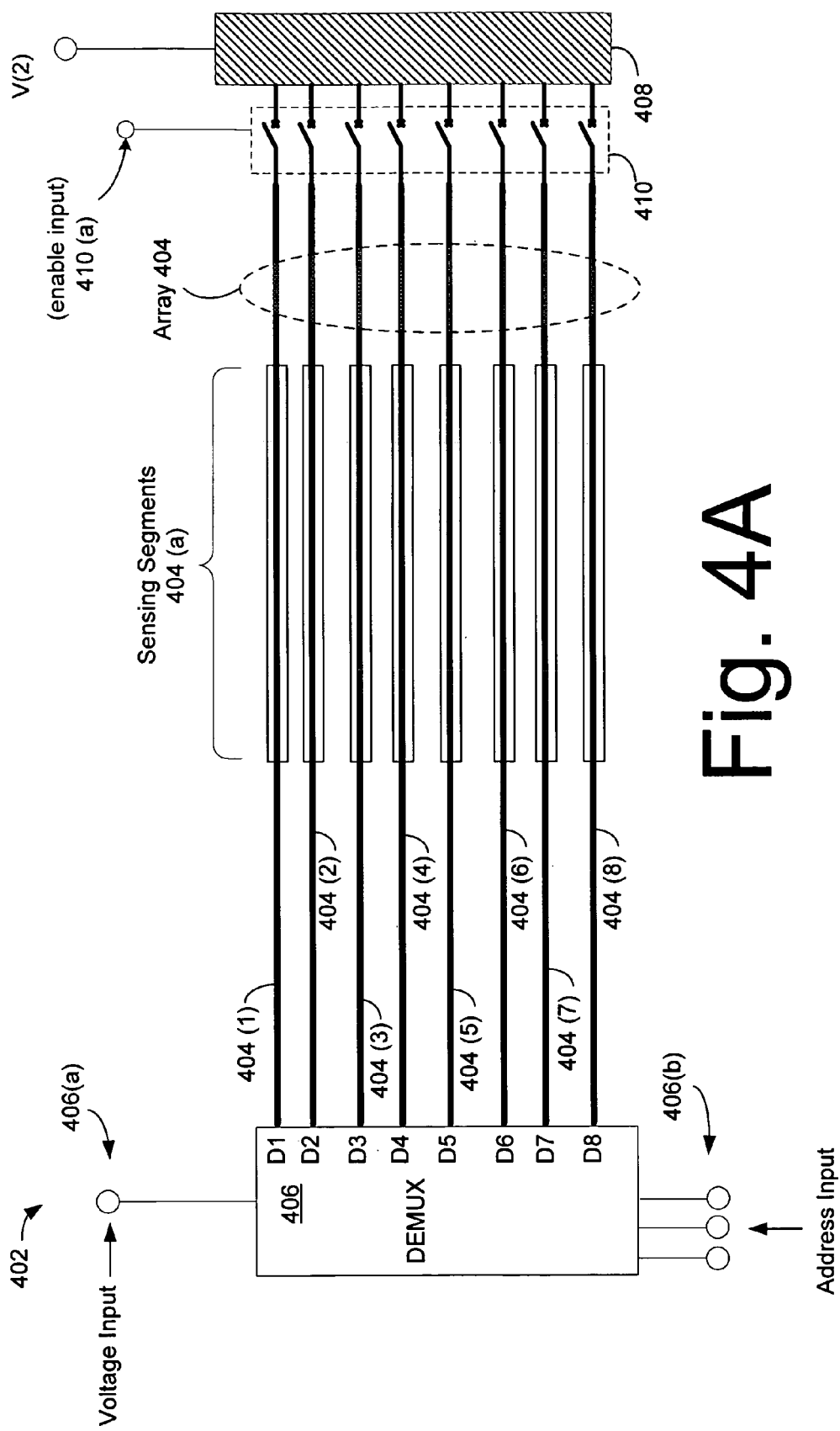
FIG. 4A is a high level schematic diagram of a nanowire based sensing system according to an embodiment of the invention.

FIG. 4A is a high level schematic diagram of a nanowire based (ChemFET) sensing system 402 that incorporates yet another embodiment of the invention. As indicated, the sensing system 402, in this embodiment, includes an array of "N" nanowires 404. To simplify the following description, we will assume that the value of "N" is eight. In other implementations, however, N may be any number, including a much greater number. The pitch of the nanowire array 404 may be smaller than 10 microns, 1000 nms, 100 nms or even approximately 10 nms, for example.

For the following discussion, we will assume that each of the nanowires in the array 404 is formed from a semiconductor material, is disposed on an insulating substrate and includes a sensing segment (i.e., sensing segments 404(a)). Furthermore, each of the nanowire sensing segments 404(a) includes an exposed surface area that is intended to be functionalized.

The sensing system 402 further includes, in this example embodiment, a demultiplexer (DEMUX) 406, a common electrode 408 and an "array switching system" 410. As shown, each of the nanowires 404 is coupled to a different output (D1-D8) of the Demux 406 and, at an opposite end, to the common electrode 408. The DEMUX 406 includes an input line 406(a), a set of address lines 406(b) and is configured to apply, through its D1-D8 outputs, an input voltage (received via the input line 406(a) ) to one or more of the nanowires 404 as determined by the logic states of the address input lines 406(b). It is noted that according to one embodiment, the DEMUX 406 may be constructed as described below with reference to FIG. 6. In alternative embodiments, for example, the DEMUX 406 may be implemented as a CMOS or some other type of standard integrated circuit.

When disabled, the switching system 410 does not affect the electrical connection between the sensing segments and the common electrode 408. When, however, the switching system 410 is enabled, the switching system 410 operates to electrically disconnect each of the nanowire sensing segments 404(a) from the common electrode 408. The switching system 410 may be enabled or disabled, in this embodiment, through an input line 410(a).

For the following discussion, it is noted that when the switching system 410 is enabled, the DEMUX 406 may be operated to hold the sensing segments 404(a) of selected nanowires to an elevated potential relative to the sensing segments of other nanowires in the array. By way of example, FIG. 4B illustrates an example of how the DEMUX 406/switching system 410 may operate to hold the sensing segments of selected nanowire 404(1), 404(5) and 404(8) to a "V(1)" potential while the rest of the nanowires float, for example.

Figure 4B:
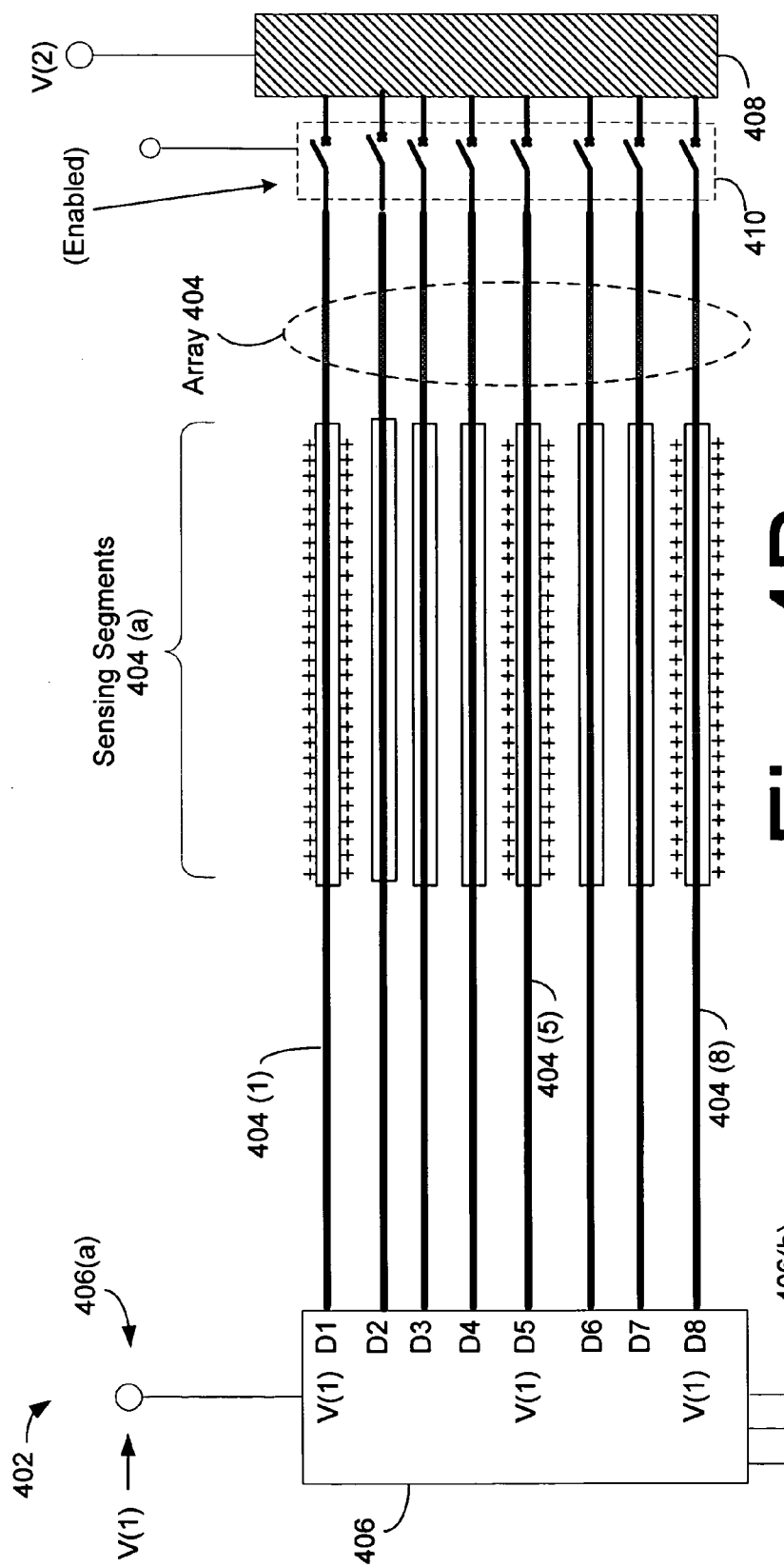
FIG. 4B illustrates one operational mode of the sensing system according to one implementation.

As indicated in FIG. 4B, the switching system 410 is enabled and, therefore, the sensing segments 404(a) are all electrically disconnected from the electrode 408. The sensing segments 404(a) remain connected, however, as shown to the corresponding DEMUX (D1-8) outputs. The V (1) potential is applied to the DEMUX input 406(a) and Address "A" is applied to the DEMUX address input 406(b). Address "A", in this example, logically selects nanowire 404(1)), nanowire 404(5) and nanowire 404(8).

The DEMUX 406 is responsive to this input by applying the V(1) potential, via the D1, D5 and D8 output, to the selected nanowires 404(1), (5) and (8). This results in charging/energizing the sensing segments of the selected nanowires (404(1), 404(5) and 404(8)) to the elevated V(1) potential. The rest of the nanowires (i.e., the unselected nanowires) are allowed to float in this embodiment. In this example, elevating the sensing segments to the V(1) potential results in the sensing segments having a positive charge relative to the unselected nanowires.

Figure 4C:
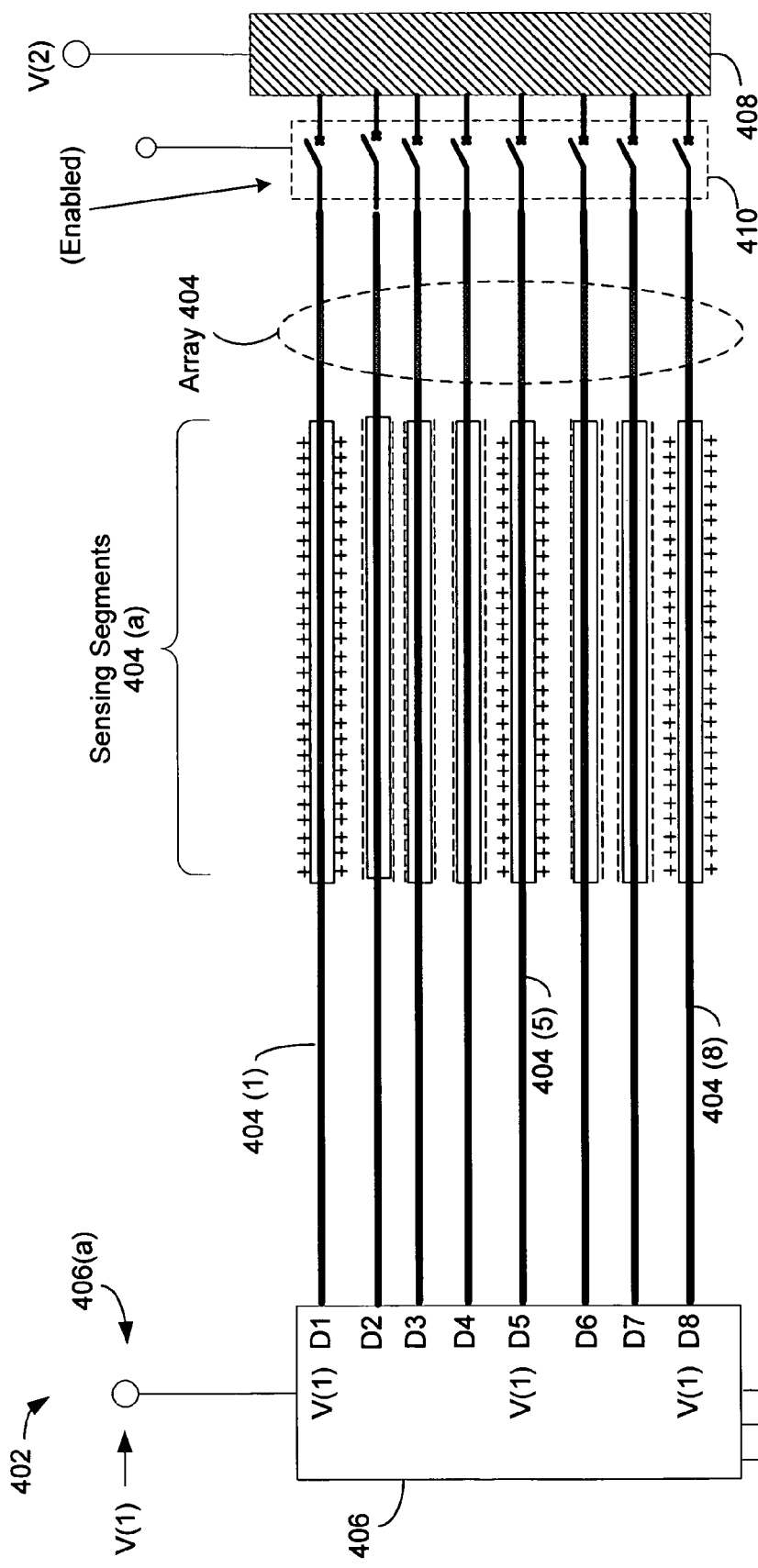
FIG. 4C illustrates one operational mode of the sensing system according to another implementation.

FIG. 4C illustrates the operation of the DEMUX 406 according to a variation of the embodiment just described. In this example, the DEMUX 406 is responsive to the same input by applying the V(1) potential, via the D1, D5 and D8 output, to the selected nanowires 404(1), (5) and (8). In this embodiment, however, the DEMUX 406 is configured to apply a potential (V(2)) to the unselected nanowires that is of opposite polarity to the V(1) input potential. This results in the sensing segments of the unselected nanowires being charged to a polarity that is opposite that of the DEMUX input potential. In example shown, the unselected nanowires are charged to a negative polarity.

The demux/switch system arrangement described above may be used for a number of purposes and embodiments of the invention are not limited to any particular purpose. By way of example, however, such an arrangement may be useful in a process to differently functionalize individual nanowires in the array 404. This proposition is illustrated further, by way of non-limiting examples, in the next part of this discussion.

Exemplary Process to Differently Functionalize an Array of Nanowires

Figure 5:
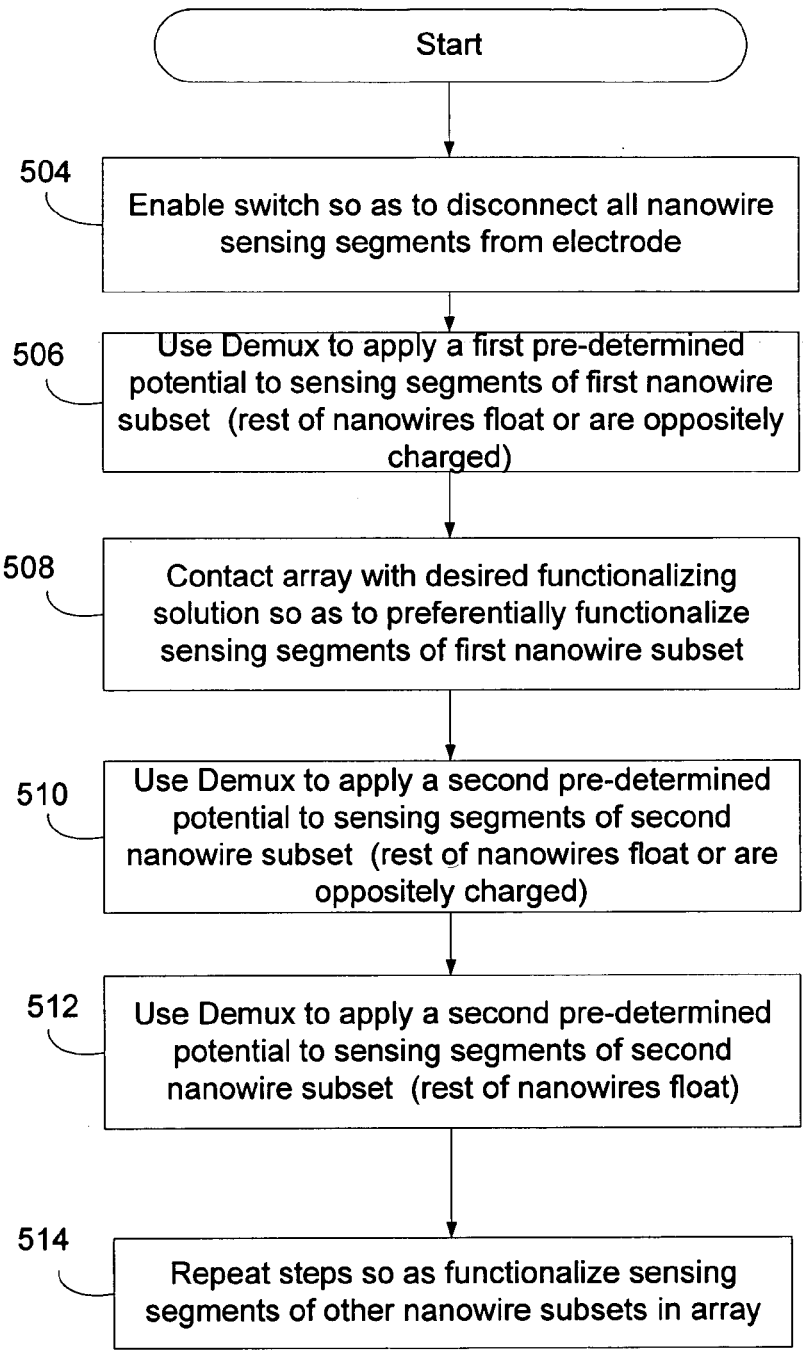
FIG. 5 is a flow diagram illustrating a process that may be followed, according to one embodiment, to differently functionalize nanowires in an array.

FIG. 5 is a flow diagram illustrating a process that may be followed, according to one embodiment, to differently functionalize nanowires in the nanowire array 404. For the next part of this discussion, we will assume the following:

Assumption #1: It is desired to functionalize the sensing segments of a first subset (nanowire subset "A") of the nanowires 404 with a first functional agent (functional agent "A");

Assumption #2: It is desired to functionalize the sensing segments of a second subset (nanowire subset "B") of the nanowires 404 with a second functional agent (functional agent "B");

Assumption #3: Nanowire subset "A" and nanowire subset "B" include different nanowires; and Assumption #4: Functional agent "A" and functional agent "B" are two different functional agents.

At step 504, the array switching system 410 is enabled so as to electrically disconnect the sensing segments 404(a) from the electrode 408. While the sensing segments are disconnected in this manner, steps 506-512 are performed.

At step 506, a pre-determined input voltage signal ("potential "A"") and the address of nanowire subset "A" are applied to the DEMUX 406. The DEMUX 406 is responsive to this input by applying potential "A" to the nanowire members of nanowire subset "A". As a result, the sensing segments of these particular nanowires are each elevated to potential "A". The DEMUX, in some implementations, may allow the rest of the nanowires (including their respective sensing segments) to float. In other implementations, the DEMUX may apply a different potential to the remaining (i.e., unselected) nanowires.

At step 508, a solution (solution "A") is brought in contact with the nanowire array 404. Solution "A" is configured to interact with the array 404 so as preferentially functionalize, with functional agent "A", those sensing segments that are presently being held to voltage potential "A" over those sensing segments that are floating and/or at a different potential. As a result of step 508 being performed, the sensing segments of nanowire subset "A" are functionalized with functional agent "A". The rest of the sensing segments are not functionalized with this particular agent and/or are coated with a minimal quantity of agent "A".

After the sensing segments of nanowire subset "A" are functionalized with functional agent "A" as just described, the process may be continued in a similar manner so as to functionalize the sensing segments of nanowire subset "B" with functional agent "B".

Accordingly, at step 510, a pre-determined input voltage signal ("potential "B"") and the address of nanowire subset "B" are applied to the DEMUX 406. The DEMUX 406 is responsive to this input by applying potential "B" to the nanowire members of nanowire subset "B". As a result, the sensing segments of these particular nanowires are each elevated to potential "B". The rest of the nanowires (including their respective sensing segments) may float. In other implementations, the DEMUX may apply a different potential (of opposite polarity) to the remaining nanowires.

At step 512, a second solution (solution "B") is brought in contact with the nanowire array 404. Solution "B" is configured to interact with the array 404 so as to preferentially functionalize, with functional agent "B", those sensing segments that are presently being held to potential "B" over those sensing segments that are floating/and or are at a different potential.

This results in modifying the array 404 so that the sensing segments of nanowire subset "B" are functionalized with functional agent "B". The rest of the sensing segments are not functionalized with this agent and/or are coated with a minimal quantity of agent "B."

As indicated by step 514, the general process just described may be further used to functionalize other subsets of the nanowires in the array with any number of different functional agents.

Example Construction of Sensing System

Figure 6:
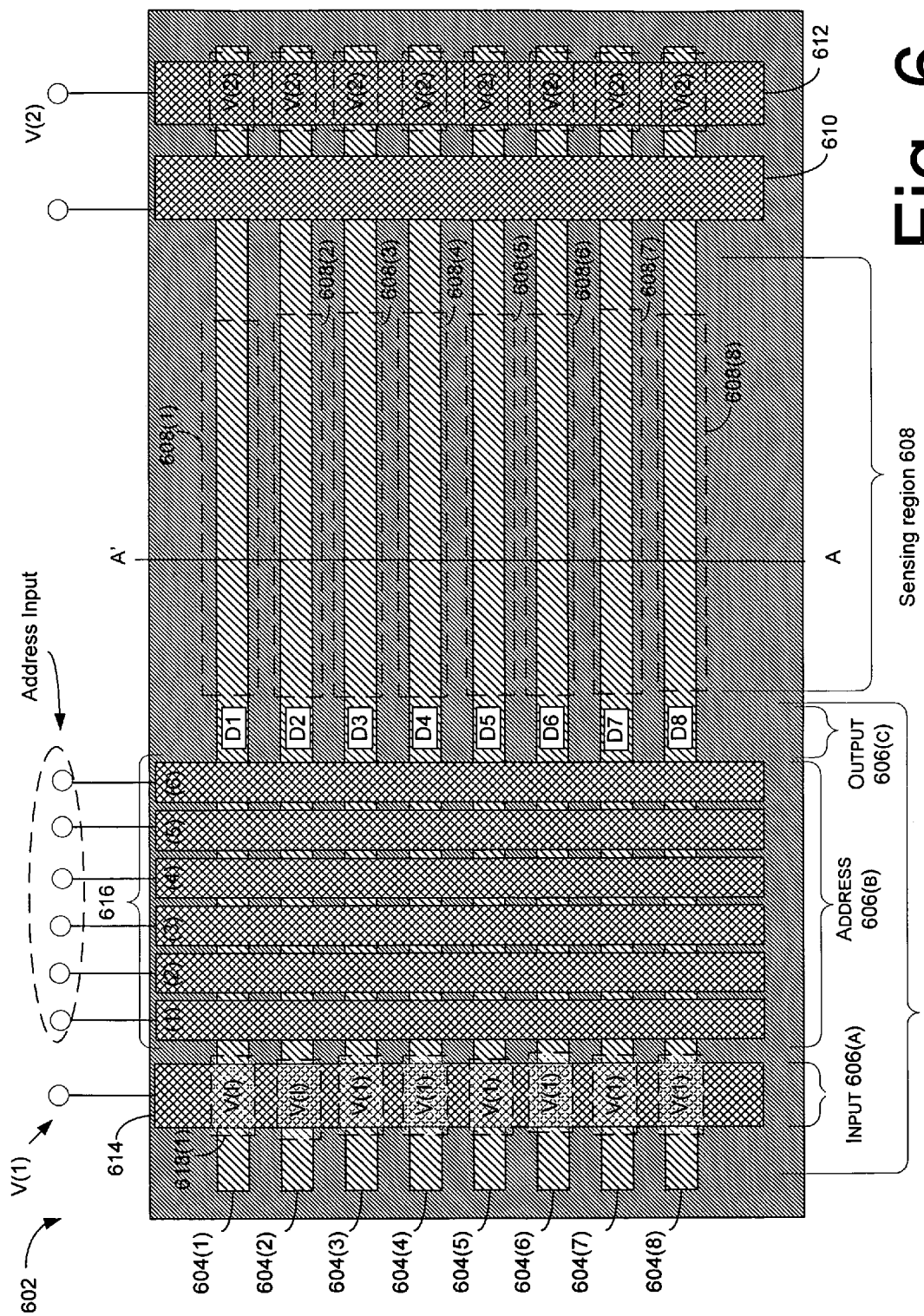
FIG. 6 is a top plan view illustrating an example how a sensing system that embodies the invention may be constructed.

FIG. 6 is a top plan view illustrating an example how variations of the sensing system just described may be constructed, according to one embodiment.

As shown, the sensing system of this example includes a cross bar arrangement 602 that includes an array of eight nanowires 604(1-8) and a set of nine elongate electrodes 614, 610, 612 and 616(1-6) that respectively cross each nanowire in the array 604 as shown.

The cross bar arrangement 602 includes, as shown, a DEMUX region 606 and a "sensing region" 608.

The nanowire array 604(1-8), in this example, may be disposed on a dielectric material, such as silicon oxide and may have a pitch that is smaller than 10 microns, 1000 nms, 100 nms or even approximately 10 nms, for example. The material of the nanowires 604 may be a semi-conductive material such as, for example, (N or P) doped silicon.

As depicted by FIG. 6, each of the nanowires 604(1-8) respectively includes a sensing segment 608(1-8) that is located within the cross bar sensing region 608.

Demux Architecture

The DEMUX region 606 generally provides the cross bar arrangement with a 1X8 DEMUX circuit. Suitable techniques for constructing such a circuit are provided by U.S. application Ser. No. 10/835,659, filed Apr. 30, 2004, entitled "FIELD-EFFECT-TRANSISTOR MULTIPLEXING/DE-MULTIPLEXING ARCHITECTURES AND METHODS OF FORMING THE SAME", by inventors Xiofeng Yang and Pavel Kornilovich. The disclosure of that application is incorporated herein by reference.

As shown, the DEMUX region 606 may logically be divided into an input region 606(a), an address region (606(b)) and an output region 606(c). To assist in the following discussion:

1.) The segment of each nanowire in the array 604 that is located within the DEMUX input region 606(a) may be referred to as the "input segment" of the nanowire;

2) The segment of each nanowire in the array 604 that is located within the DEMUX address region 606(b) may be referred to as the "address segment" of the nanowire; and 3) The segment of each nanowire in the array 604 that is located within the DEMUX output region 606(c) may be referred to as the "output segment" of the nanowire.

As shown, the DEMUX input region 606(a) includes a DEMUX input electrode 614 which is in electrical contact with the nanowire input segment of each nanowire in the array 604. The DEMUX input electrode 614 may provide an electrical contact point for a power supply system (not shown) and can be used to apply an input voltage (e.g., V(1)) to the DEMUX input region 606(a).

The address region 606(b) of this example includes six address electrodes electrodes 616(1-6) that generally provide a means for selecting one or more nanowires in the array. The address region 606(b) may include additional address electrodes which are not illustrated. In this embodiment, one or more nanowires may be selected by applying address input to the address electrodes 616(1-6) that is in accordance with a pre-determined protocol.

The address segment of each nanowire that is not selected is electrically gated (at least once) via an electric field that is generated by one or more of the address electrodes 616(1-6)). This results in the (unselected) nanowire input segment being electrically disconnected from the nanowire output segment. As a result, the DEMUX input voltage (e.g., V1) is not routed to the (unselected) nanowire output segment and corresponding sensing segment.

The address segment of each nanowire that is selected, however, is not electrically gated by any of the address electrodes and, therefore, the nanowire output segment and input segment remain electrically connected (through the address segment of the nanowire). Consequently, the DEMUX input voltage (e.g., V(1)) is routed to the output segment and sensing segment of each selected nanowire.

Figure 7:
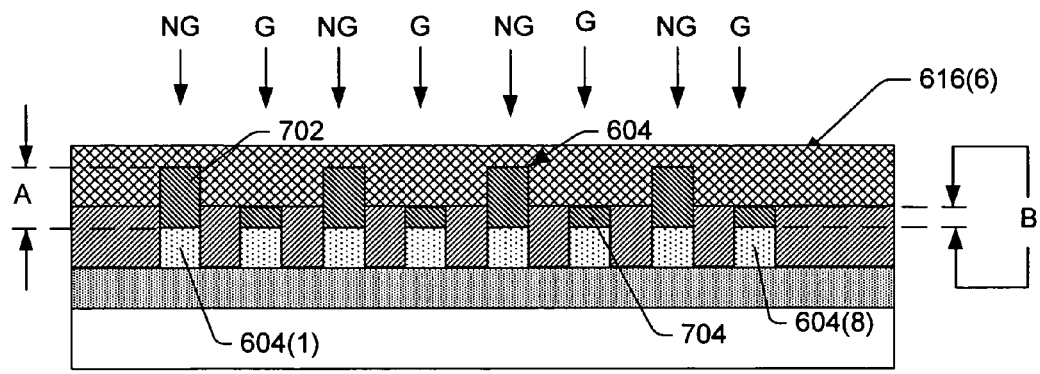
FIG. 7 illustrates a cross-section along the elongate dimension of a DEMUX address electrode according to one embodiment.

Referring now also to FIG. 7, a cross-section along the elongate dimension of a representative one of the DEMUX address electrodes (i.e., in this example address electrode 616(6)) is shown.

As indicated in FIG. 7, a dielectric structure is located between each nanowire 604(1-8) and the address electrode 616(6). The dielectric structures are generally of one of two thicknesses: thickness "A" or thickness "B", wherein thickness "A" is greater than thickness "B". First dielectric structure 702, for example, corresponds to thickness "A" and is interposed between the nanowire 604(1) and the address electrode 616(6). The second dielectric structure 704, for example, corresponds to thickness "B" and is interposed between the nanowire 604(8), for example.

Moreover, in operation, an address input (in the form of a pre-determined voltage) may be placed on the address input electrode 608(3) and, as a result, the electrode 608(3) generates an electric field. The electric field is effective to electrically "gate" a nanowire through the thinner dielectric structure (i.e., thickness "B"). The electric field is not effective, however, to gate a nanowire through the thicker dielectric structure (i.e., thickness "A"). Accordingly, the thickness of the dielectric between each address electrode and each respective nanowire can be selected so as to implement the DEMUX address protocol.

As illustrated in FIG. 7, in the example shown, the electric field generated by the address electrode 608(3) is not effective to electrically gate nanowires 604(1), (3), (5) and (7) through the corresponding thicker dielectric structures. The electrical field is, however, effective to electrically gate nanowires 604(2), (4) and (8) through the corresponding thinner dielectric structures.

Figure 8:
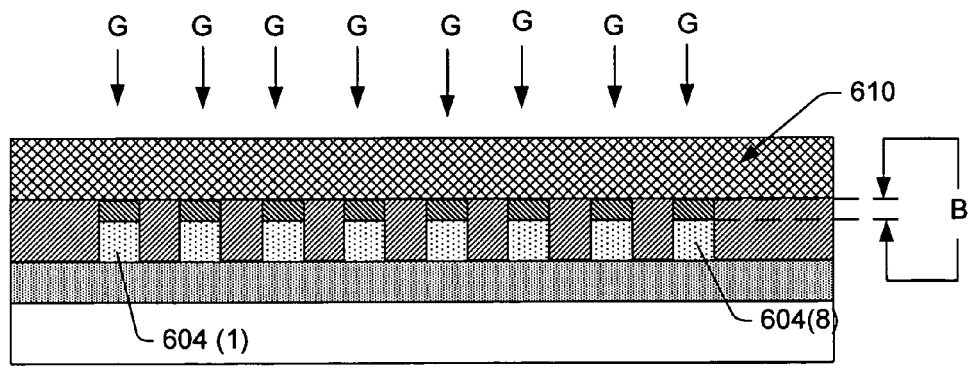
FIG. 8 illustrates a cross-section along the elongate dimension of a gate electrode according to one embodiment.

Referring now also to FIG. 8, a cross-section along the elongate dimension of another electrode (gate electrode 610) is shown. As shown, located between the gate electrode 610 and each nanowire is a dielectric structure of the thinner thickness (i.e., thickness "B"). Moreover, when a suitable voltage is applied to the gate electrode 610, the gate electrode 610 generates an electric field that electrically gates each of the nanowires 604 in the region that is overlapped/crossed by the gate electrode 610. In this manner, the gate electrode 610 can be used to electrically disconnect the sensing segment of each nanowire 604 from the (common) electrode 612. Accordingly, the gate electrode represents one embodiment of an array switching system as described and illustrated above in FIG. 4A.

As previously noted, the DEMUX input electrode 614 may provide a contact point for an external power supply system. It is further noted that the common electrode 612 may provide a second contact point for the external power supply system as well as a monitoring system (not shown) that is capable of monitoring an electrical property of each nanowire during a sensing operation, as is described further below.

Figure 9:
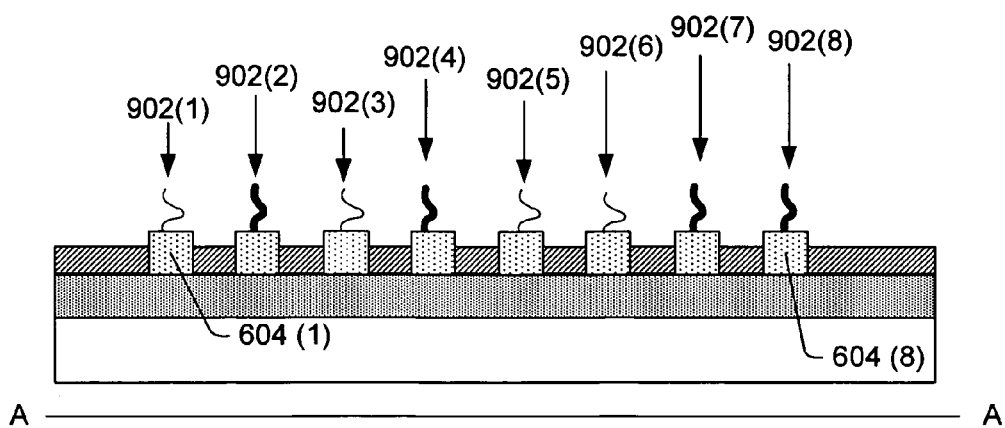
FIG. 9 illustrates a cross-section along line A-A' of FIG. 6.

Referring now also to FIG. 9, a cross-section of the nanowire sensing segment along line A-A' of FIG. 6 is shown according to one embodiment. In this example, we assume the nanowire sensing segments have been differently functionalized by the methods described above and by using the DEMUX ability provided by the DEMUX region 606 along with the capability provided by the gate electrode 610 to disconnect the array of nanowires 604 from the common electrode 612. For example, the nanowire sensing segment 604(1) is functionalized with a coupling agent and is further functionalized with a binding agent linked to the coupling agent, the functional ensemble being indicated in FIG. 9 as 902(1). The nanowire sensing segment 604(8) is functionalized with the same coupling agent and is functionalized with a different binding agent linked to the coupling agent, the ensemble of functional agents being indicated as 902(8).

The binding agents in this non-limiting example are single-stranded DNA oligonucleotide probe molecules that differ only in their sequence of bases (e.g., ACGTAACCG-GTTACGTTGCA and CGAATCGGATAGCCCTATGG). In this or another sensing system, nanowire sensing segments may be functionalized differently with any number of antibodies and/or nucleic acid binding agents and/or other functional agents that are adapted for the present purposes of functionalization, coupling, binding, and/or sensing.

Operation of Sensing System

Figure 10A:
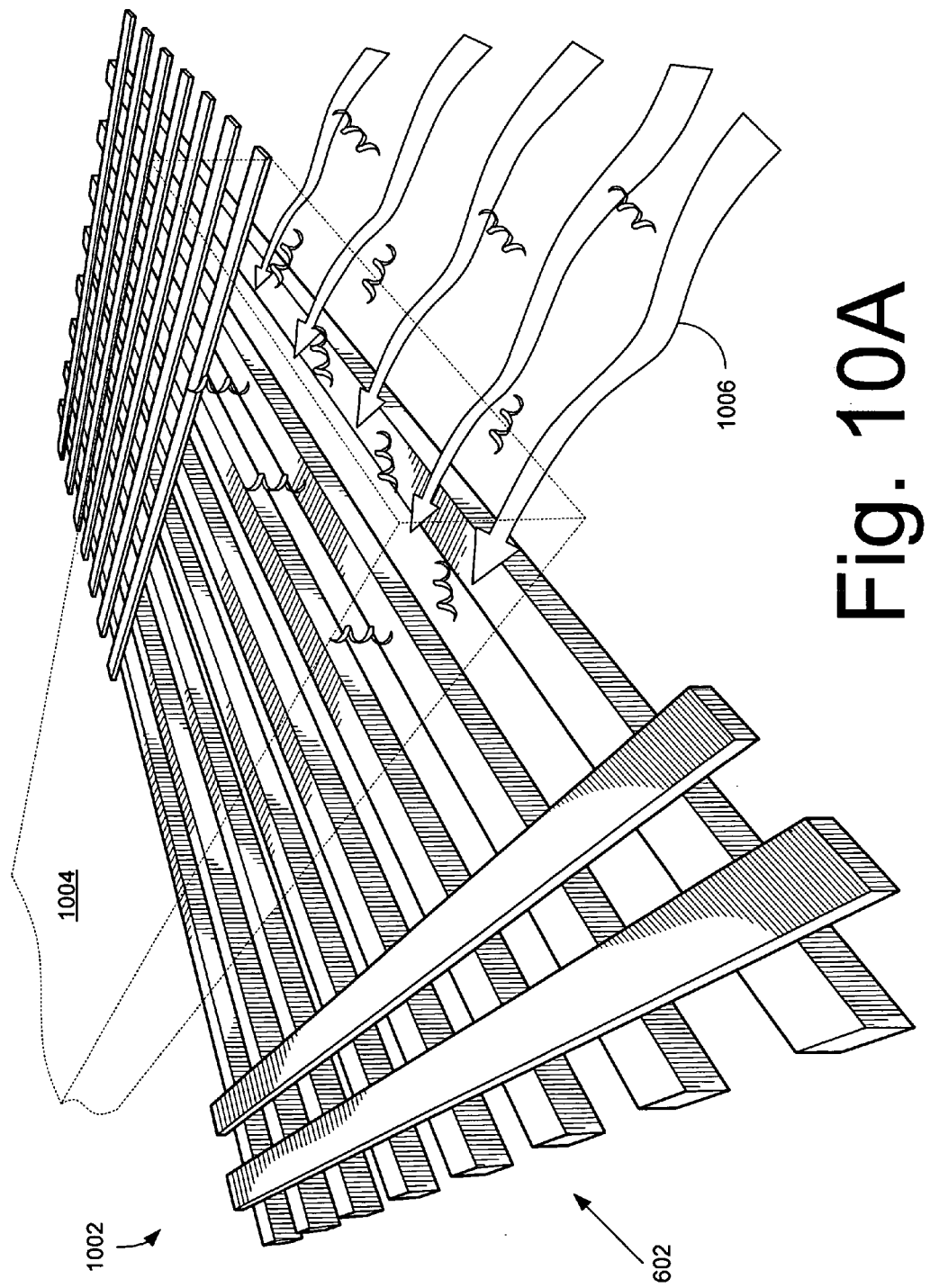
FIG. 10A is an abstract diagram illustrating a sensing system according to one embodiment.

FIG. 10A is an abstract diagram illustrating further a sensing system 1002 that may incorporate the cross bar arrangement 602 in one example. As shown, the cross-bar arrangement 602 may be integrated with a fluid handing system 1004 which is used to contact nanowire sensing segments with fluid materials (e.g., fluid materials 1006). During a functionalization process, the fluid materials may be configured to functionalize the sensing segment of one or more of the nanowires 604 as described above. During a sensing operation, the fluid materials 1006 may be the sample that is under analysis.

In the embodiment shown, the fluid handling system 1004 may include, for example, an integrated micro-fluidic channel system for controllably moving a fluid from a source to the sensing segments of the nanowires 604. Examples of such fluidic systems are generally described in the patent literature. See, for example, the patents assigned to Caliper Technologies Corporation. In other embodiments, for example, the fluid handling system 1004 may comprise a fluid reservoir that is in fluidic communication with the sensing segments of the nanowires 604.

It is further noted that the fluid handling system 1004 may be integrated with a pipetting system (not shown) for transferring fluids from storage vessels to the fluid handling system 1004. The pipetting system may include one or more automated robotic armatures, for example, for moving pipettors from the storage vessels to the fluid handling system 1004.

Figure 10B:
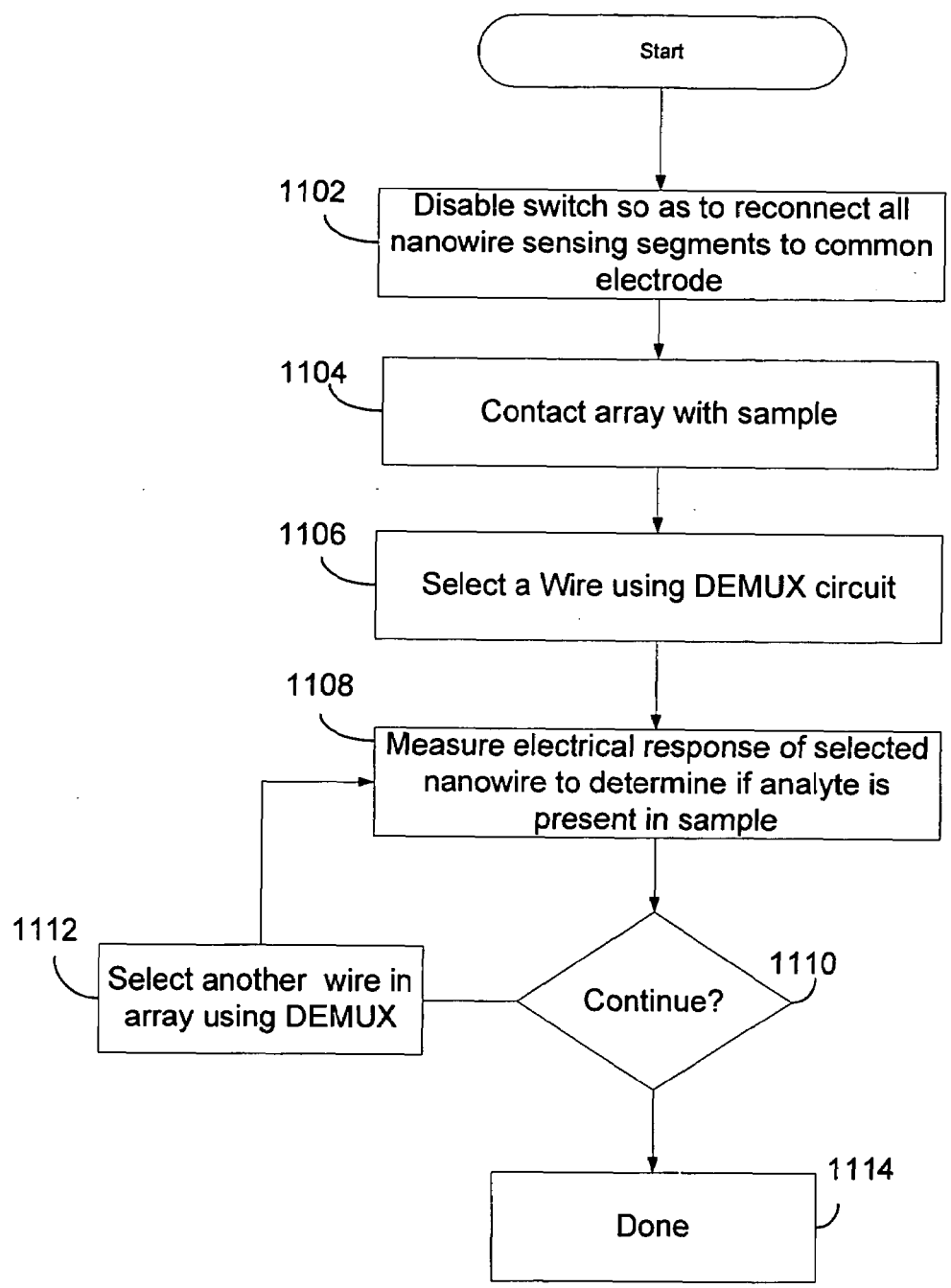
FIG. 10B is a flow diagram illustrating an example operation of the sensing system according to one embodiment.

FIG. 10B is a flow diagram illustrating an example operation of the sensing system 1002 to test a sample fluid. We assume in this non-limiting example that the sensing segment of each nanowire in the array 604 is functionalized to detect a different analyte so to provide the sensing system 1002 with the capability to detect the presence of eight different analytes (1-8) in a sample. Nanowire 604(1), for example functionalized to detect the presence analyte (1), Nanowire 604(2) is functionalized to detect the presence of analyte (2), etc.

Beginning at step 1102, the array switching system (i.e., the gate electrode 610) is "disabled" so as to electrically reconnect the array of nanowires 604(1-8) to the common electrode 612. This step may be performed, for example, by configuring the gate electrode 610 so that it no longer generates an electric field that is effective to gate the nanowires 604.

At step 1104, the sensing segments 608(1-8) of the nanowire array 604 is placed in contact with a desired fluid sample that is to be tested. This step may include introducing the sample into the fluid handling system 1004 and permitting the sample to pass through the fluid handling system 1004.

At step 1106, nanowire 604(1) is selected to test by applying the address of that particular nanowire to the DEMUX 606. The rest of the nanowires (i.e., nanowires 604(2-8)) remain unselected. The DEMUX 606 is responsive to this input by:

1) Providing a closed electrical connection, through the body of the nanowire 604(1), between the input electrode 614 and the common electrode 612; and 2) Providing an open electrical connection, through the body of each unselected nanowire, between the input electrode 614 and the common electrode.

At step 1108, an electrical property (e.g., electrical conductance and/or resistance) of the selected nanowire 604(1) is measured in order to determine if analyte (1) is present in the sample. This step may be accomplished by applying a potential difference across the input electrode 614 and the common electrode 612 and then measuring the resulting current passing through the nanowire 604(1).

At steps 1110, 1112 another nanowire (e.g., nanowire 604(2)) in the array is selected and measured in the same manner. Steps 1110, 1112 may be repeated as desired in order to determine if the sample being tested includes any of the analytes (1-8).

It is noted that although the flow charts described above show a specific order of execution, it is understood that the order of execution may differ from that which is depicted. For example, the order of execution of two or more blocks/steps may be scrambled relative to the order shown. Also, two or more blocks/steps shown in succession in the flow charts may be executed concurrently or with partial concurrence. It is understood that all such variations are within the scope of the present invention.

Many variations and modifications may be made to the above-described embodiment(s) of the invention without departing substantially from the spirit and principles of the invention. For example, in the above description sensing systems that use employ one or more nanowires are described. It is to be understood, however, that sensing systems that employ microscale wires may embody the invention and the processes described above may be used to functionalize microscale wires in various embodiments of the invention. For example, a sensing system that employs a wire that has a cross section less than one millimeter may embody the invention. Moreover, all such modifications and variations are intended to be included herein within the scope of the present invention.

What is claimed:

1. A method of functionalizing a nanowire in a CHEM-FET sensing system, the nanowire being connected at one part to a first electrode and at an opposite part to a second electrode, the method comprising:
   gating current at a pre-determined location of the nanowire so that a segment of the nanowire is electrically disconnected from the second electrode but remains electrically connected to the first electrode;
   applying a potential to the first electrode in order to produce a charge on an exposed area of the nanowire segment;
   contacting the nanowire segment with a solution configured to functionalize the charged exposed area with a functional agent, so as to functionalize the nanowire;
   wherein the contacting step is at least partially performed while also performing the gating and applying steps.

2. The method of claim 1, wherein the gating step includes gating current at a pre-determined location of the nanowire so that a potential applied to the first electrode while the segment of the nanowire is disconnected from the second electrode produces a uniform charge on the exposed area of the nanowire segment.

3. The method of claim 1, wherein the gating step comprises:
   generating an electric field that produces a localized field effect within a region of the nanowire located between the nanowire segment and the second electrode but not within a region of the nanowire located between the nanowire segment and the first electrode, where the field effect prevents current from passing between the nanowire segment and the second electrode.

4. The method of claim 1, wherein the gating step comprises:
   operating a field effect transistor to generate an electric field that is effective to prevent current from passing between the nanowire segment and the second electrode but does not prevent the nanowire segment from taking a charge substantially equal to the electric potential of the first electrode.

5. The method of claim 1,
   where the solution is an electrolyte;
   where the gating and applying steps result in producing a uniform charge on the exposed area of the nanowire segment; and
   where the contacting step results in electroplating the charged exposed area with a metal functional agent.

6. The method of claim 1, wherein the solution comprises a functional agent that is charged to a polarity that is opposite that of the charge produced on the exposed area of the nanowire segment.

7. The method of claim 1, wherein the functional agent is configured to bind with a target analyte.

8. The method of claim 1, wherein the functional agent is configured to bind with a target DNA molecule.

9. The method of claim 1, wherein the functional agent is configured to bind with a biological species, wherein the biological species is a thiol group, a peptide nucleic acid or a Ribonucleic acid.

10. The method of claim 1, wherein the functional agent is configured to bind with one of an aptamer, a hormone, a carbohydrate, a protein, an antibody, an antigens or a molecular receptor.

11. The method of claim 1, wherein the functional agent is configured to bind with a second functional agent and the method further comprises:
    further functionalizing the nanowire segment with the second functional agent.

12. The method of claim 1, further comprising:
    electrically reconnecting the nanowire segment to the second electrode;
    exposing the nanowire segment to a fluid sample that is to be tested;
    monitoring for a change in an electrical property of the nanowire to determine if a target analyte is present in the sample.

13. A method of functionalizing an array of nanowires in a CHEMFET sensing system, where each nanowire includes a sensing segment that is electrically connected to a common electrode, the method comprising:
    electrically disconnecting each nanowire sensing segment from the common electrode;
    applying a first potential to the sensing segment of at least one selected nanowire in the array;
    contacting the sensing segment of each nanowire in the array with a first solution configured to functionalize those sensing segments that are presently being held to the first potential with a functional agent, so as to functionalize those sensing segments that are presently being held to the first potential with a functional agent;
    wherein the contacting step is at least partially performed while each nanowire is electrically disconnected from the common electrode and while applying the first potential.

14. The method of claim 13, further comprising:
    applying a second potential to the sensing segment of at least one nanowire in the array;
    wherein the second potential is of opposite polarity with respect to the polarity of the first potential;
    wherein the contacting step is at least partially performed while performing both the first and second potential applying steps.

15. The method of claim 13, wherein the solution comprises an electrolyte solution configured to electroplate a sensing segment being held to the first potential with a metal functional agent.

16. The method of claim 13, wherein the solution comprises the functional agent electrically charged to a polarity that is opposite that of the first potential polarity.

17. The method of claim 13, wherein the contacting step results in those sensing segments being held to the first potential being functionalized with the functional agent.

18. The method of claim 17, wherein the functional agent is configured to bind with a target analyte.

19. The method of claim 17, wherein the functional agent is configured to bind with a target DNA molecule.

20. The method of claim 17, wherein the functional agent is configured to bind with one of a thiol group, a peptide nucleic acid or a Ribonucleic acid.

21. The method of claim 17, wherein the functional agent is configured to bind with one of an aptamer, a hormone, a carbohydrate, a protein, an antibody, an antigen or a molecular receptor.

22. The method of claim 17, wherein the functional agent is configured to bind with a second functional agent and the method further comprises:
further functionalizing the nanowire segment with the second functional agent.

23. The method of claim 22, wherein the functional agent comprises carboxylate silane.

24. The method of claim 17, wherein the contacting step comprises:
permitting the solution to flow through a microfluidic channel that houses the sensing segment of each nanowire in the array.

25. The method of claim 13, further comprising:
electrically reconnecting each nanowire sensing segment of each nanowire to the common electrode;
exposing each nanowire sensing segment of each nanowire to a sample;
monitoring for a change in an electrical property of the at least one selected nanowire in the array to determine if a target analyte is present in the sample.

26. A method of functionalizing an array of nanowires in a CHEMFET sensing system, where each nanowire has a sensing segment and is connected at one part to a first electrode and at an opposite part to a common electrode, the method comprising:
disconnecting each nanowire of each sensing segment from the common electrode;
applying a first potential of pre-determined polarity to the sensing segment of at least a first nanowire in the array so as to create a potential difference between the sensing segment of the first nanowire and the sensing segment of at least one other nanowire in the array;
contacting the sensing segment of each nanowire in the army with a solution that is configured to functionalize those sensing segments being held to the first potential with a functional agent, so as functionalize those sensing segments being held to the first potential;
wherein the contacting step is at least partially performed while each nanowire is electrically disconnected from the common electrode and while applying the first potential.

27. The method of claim 26, wherein the functional agent is electrically charged in the solution to a polarity that is opposite that of the first potential polarity.

28. The method of claim 27, further comprising:
reconnecting each nanowire of each sensing segment to the common electrode; then
using the CHEMFET sensing system to determine it an analyte is present in a sample.

* * * * *

UNITED STATES PATENT AND TRADEMARK OFFICE
CERTIFICATE OF CORRECTION

| | |
|---|---|
| PATENT NO. | : 7,335,526 B2 |
| APPLICATION NO. | : 11/263788 |
| DATED | : February 26, 2008 |
| INVENTOR(S) | : Kevin F. Peters et al. |

Page 1 of 1

It is certified that error appears in the above-identified patent and that said Letters Patent is hereby corrected as shown below:

In column 16, line 15, in Claim 26, delete "army" and insert -- array --, therefor.

In column 16, line 31, in Claim 28, delete "it" and insert -- if --, therefor.

Signed and Sealed this

Nineteenth Day of August, 2008

JON W. DUDAS
*Director of the United States Patent and Trademark Office*